United States Patent [19]

Elgavish et al.

[11] Patent Number: 5,242,681
[45] Date of Patent: Sep. 7, 1993

[54] LIPOPHILIC CONTRAST AGENTS FOR DIAGNOSTIC IMAGE ANALYSIS

[75] Inventors: Gabriel A. Elgavish, Hoover; Sung K. Kim, Birmingham, both of Ala.

[73] Assignee: Research Corporation Technologies, Inc., Tucson, Ariz.

[21] Appl. No.: 925,352

[22] Filed: Aug. 4, 1992

Related U.S. Application Data

[62] Division of Ser. No. 492,519, Mar. 12, 1990, Pat. No. 5,154,914.

[51] Int. Cl.$^5$ .............. G01N 24/08; A61K 49/04; A61K 31/28; A61K 31/295
[52] U.S. Cl. .............................. 424/4; 424/9; 436/173; 128/653.4; 514/492; 514/502; 514/550; 514/836; 534/16; 556/44; 556/50; 556/63; 556/107; 556/117; 556/134; 556/148
[58] Field of Search ............... 424/4, 9; 514/558, 592, 514/502, 563, 836; 436/173; 128/653.4, 654; 534/16; 556/44, 50, 107, 148, 134, 63, 117

[56] References Cited

U.S. PATENT DOCUMENTS 4,647,447  3/1987  Gries et al. .............................. 424/9
4,826,673  5/1989  Dean et al. ............................. 424/9

FOREIGN PATENT DOCUMENTS 0250358  12/1987  European Pat. Off. .
1120384  5/1989  Japan .

OTHER PUBLICATIONS

Cupkova, V. Chem. Abstracts CA112(1):4197y (1990).
Devinsky Chem. Abstracts CA102(26):226400s (1985).
Yaroshenko, G. F., et al. (1974) Synthesis of aminopolycarboxylic acid esters. Chemical Abstracts, vol. 80, 1974:478, Abstract 133388f.
Kabaika, G. W. et al., (1989) Gadolinium-labeled liposomes containing paramagnetic amphiphathic agents: targeted MRI contrast agents for the liver., Chem. Abstract: 8–Radiation, vol. 110, 283.
Guilmette, Raymond A., et al. (1979) Synthesis and therapeutic testing of mono–and dialkyl esters of pentetic (diethylenetriaminepentaacetic) acid for decorporation of polymeric plutonium, Chem. Abstract 90:567, Abstract #203405c.
Schaefer, Paul, (1974) Diester-amine adducts as fabric softeners, Chem. Abstract 81:Abstract 51056c.
Tilcock, "Liposomal Gd–DTPA: Preparation and Characterization of Relaxivity," (1989) Radiology 171: 77–80.

Primary Examiner—Glennon H. Hollrah
Assistant Examiner—Gary E. Hollinden
Attorney, Agent, or Firm—Scully, Scott, Murphy & Presser

[57] ABSTRACT

The present invention relates to contrast enhancing agents, conjugates thereof, pharmaceutical compositions thereof, and methods for diagnostic analysis, particularly NMR image analysis using these agents. The contrast enhancing agents are chelates of paramagnetic, ferromagnetic or diamagnetic metal ion(s) complexed with new lipophilic complexing acids related to polyaminopolycarboxylic acids.

23 Claims, No Drawings

LIPOPHILIC CONTRAST AGENTS FOR DIAGNOSTIC IMAGE ANALYSIS

This invention was made with U.S. Government support under grant number HL-33200 awarded by the National Institutes of Health. The U.S. Government has certain rights in the invention.

This is a divisional of copending application Ser. No. 492,519, filed on Mar. 12, 1990, now U.S. Pat. No. 5,154,914.

FIELD OF THE INVENTION

The loss of detail in NMR spectra or lack of sufficient contrast in NMR images can limit the use of NMR analysis. Contrast agents have been employed in order to improve NMR imaging for non-invasive clinical diagnoses of mammalian hosts. The present invention relates to a class of compositions and a method for NMR imaging using NMR signal affecting amounts of a paramagnetic, diamagnetic or ferromagnetic metal ion chelated with a new lipophilic contrast agent, which are preferably new iminopolycarboxylate derivatives of fatty acids. Moreover, these compositions are also useful for X-ray image analysis and in ultrasonic contrast analysis.

BACKGROUND OF THE INVENTION

Diagnostic imaging has emerged in recent years as a superior technique for noninvasive clinical diagnosis of heart, brain, kidney and other organs and tissues in mammalian hosts. Nuclear magnetic resonance (NMR) analysis, or magnetic resonance imaging (MRI), in many instances, requires contrast enhancement to obtain useful images which delineate various aspects of the tissue, especially normal as contrasted with abnormal tissue.

The techniques of MRI or NMR imaging encompass the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

The prior art discloses various techniques that can be employed for affecting an NMR signal in a host, of which a common technique is to introduce into the host a paramagnetic substance prior to NMR analysis which advantageously affects contrast, or selectively shifts the NMR signal. A large variety of compounds have found use in NMR and X-ray image analysis or as shift reagents.

New compounds with low toxicity in vivo, high relaxivity, tissue and pathology specificity, and sufficient tissue retention time but complete eventual clearance are being sought. The well known ethylenediaminetetraacetic acid (EDTA) and diethylenetriaminepentaacetic acid (DTPA) complexes with gadolinium (Gd) show low toxicity in vivo and rapid clearance rates but do not exhibit strong tissue specificity and long enough retention time, especially for myocardial tissue. Also their relaxivity decreases at hig magnetic fields already being introduced into the industry. Accordingly, contrast enhancing agents with higher relaxivity, positive field profile, greater tissue specificity and sufficient tissue retention time in addition to low toxicity are needed. One approach has been to modify EDTA and DTPA to achieve these goals.

U.S. Pat. No. 4,647,447 reports chelating agents for NMR analysis which include EDTA derivatives and DTPA derivatives differing significantly from the present invention because they lack the lipophilic fatty acid moiety of the subject invention, and because of their inherently negative field profiles.

Several additional EDTA and DTPA derivatives are disclosed in U.S. Pat. Nos. 4,687,658; 4,687,659; 4,746,507; 4,804,529 and 4,822,594. Collectively, these patents report ester, amide and polysaccharide derivatives suitable for general MRI analysis but which, nevertheless do not have the fatty acid derivatives and positive field profiles of the present invention.

Fatty acids and fatty acid analogs have been reported to accumulate in myocardial tissue when administered as radiopharmaceuticals. U.S. Pat. No. 4,763,358 discloses that branched chain fatty acids have utility in cardiac imaging using radioactive iodine as the contrast moiety.

In a study of the biological distribution of chemical analogs of fatty acids and long chain hydrocarbons containing a strong chelating agent, Karesh, S. M. et al. (1977) *J. Pharm. Sci* 66: 225–228, describe radiopharmaceutical cobalt (Co) and technicium (Tc) complexes wherein the alkyl end of a fatty acid molecule is covalently bound to a carboxyl group on the chelating agent, forming an ester derivative of the chelating agent. In contrast, the subject chelating agents are ester derivatives of the fatty acid and will therefore be more lipophilic due to the long, free alkyl chain then the Karesh compounds which exhibit significant hydrophilic character due to the free carboxylic acid ends. Moreover, Karesh reports that the compounds under investigation studied were not sufficient biological analogs to act as tracers for fatty acid metabolism in the myocardium.

Accordingly, the present invention provides contrast enhancing agents for diagnostic image analysis which are lipophilic in nature because of a free hydrocarbon chain coupled via an ester linkage with a strong chelating agent, such as polyaminopolycarboxylic acid derivatives, especially EDTA and DTPA derivatives.

SUMMARY OF THE INVENTION

This invention relates to lipophilic contrast enhancing agents for diagnostic image analysis, preferably for NMR or MRI analysis, but which also find utility in X-ray image analysis and ultrasonic analysis. While generally described as contrast enhancing agents, it is understood that these agents can also act as NMR shift reagents. Specifically, therefore, the contrast enhancing agents are complexing acids, or a salt thereof, and at least one paramagnetic, diamagnetic or ferromagnetic metal ion, with the complexing acids having at least one fatty acid chain as represented by the formula

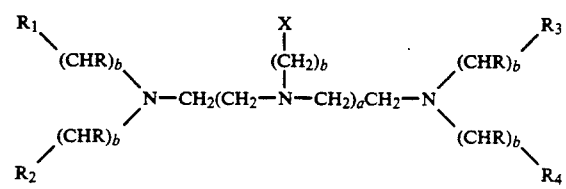

wherein a is 0 to 5;
b is 1 to 5;
each of a and b can be the same or different;
each R is the same or different and is hydrogen, lower alkyl, hydroxy, halo, lower alkoxy, aryl, or lower aralkyl;
at least one of $R_1$, $R_2$, $R_3$, $R_4$ or X has the formula

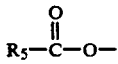

wherein $R_5$ is a saturated or unsaturated hydrocarbon chain having 6 to 30 carbon atoms; and the others of $R_1$, $R_2$, $R_3$, $R_4$ or X are hydrogen, hydroxyl, —$COOR_6$, —$CONR_7 R_8$ or a chelating moiety,
wherein $R_6$, $R_7$, and $R_8$ are the same or different and represent hydrogen, lower alkyl, lower alkoxy, lower carboxyalkylene, or a chelating moiety.

The preferred compounds are polyaminopolycarboxylic acids derivatives, especially EDTA derivatives having one or two fatty acid moieties as provided above, and having a carboxymethylacetamide replacing at least one acetic acid group, and even more preferably replacing two acetic acid groups. Other preferred compounds are DTPA derivatives having at least one fatty acid moiety as provided above.

Conjugates of the contrast enhancing agents of the present invention are also provided. Liposomes, proteins, peptides, antibodies, and other physiological agents can be conjugated with contrast enhancing agents for diagnostic image analysis.

Another aspect of the invention is directed to a method for diagnostic analysis by administering the subject contrast enhancing agents or conjugates thereof to a host, preferably a mammalian host, in an amount sufficient to effect the desired contrast and then subjecting the host to diagnostic analysis. Preferably diagnostic analysis is NMR analysis; including and especially preferred, NMR imaging analysis (or MRI). Further, the subject compounds are useful in diagnostic analysis by X-ray image analysis or ultrasonic analysis.

A further aspect contemplated by the instant invention is a method of tissue specific imaging with a tissue-specific contrast enhancing agent as provided herein.

Yet another aspect of the invention provides pharmaceutical compositions containing the subject contrast enhancing agents or conjugates thereof and a pharmaceutically acceptable carrier.

DETAILED DESCRIPTION OF THE INVENTION

The present invention is directed to complexing acids and salts thereof which when combined with a paramagnetic, ferromagnetic or diamagnetic metal ion form contrast enhancing agents, wherein the acids are represented by the formula

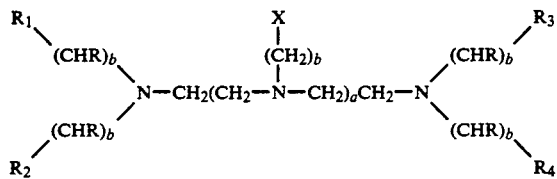

wherein
a is 0 to 5;
b is 1 to 5;
each of a and b can be the same or different;
each R is the same or different and is hydrogen, lower alkyl, hydroxy, halo, lower alkoxy, aryl, or lower aralkyl;
at least one of $R_1$, $R_2$, $R_3$, $R_4$ or X has the formula

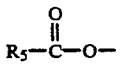

wherein $R_5$ is a saturated or unsaturated hydrocarbon chain having 6 to 30 carbon atoms; and the others of $R_1$, $R_2$, $R_3$, $R_4$ or X are hydrogen, hydroxyl, —$COOR_6$, —$CONR_7 R_8$ or a chelating moiety
wherein $R_6$, $R_7$, and $R_8$ are the same or different and represent hydrogen, lower alkyl, lower alkoxy, lower carboxyalkylene, or a chelating moiety.

By "complexing acid" herein is meant an acid and may include a Lewis acid, which acts as a ligand for the metals of interest thereby forming a chelate.

As used herein, the term lower alkyl, when used singly or in combination, refer to alkyl groups containing one to six carbon atoms. They may be straight chain or branched and include such groups as methyl, ethyl, propyl, isopropyl, butyl, sec-butyl, isobutyl, t-butyl, pentyl, isopentyl, neopentyl, hexyl and the like. The preferred alkyl groups contain one to four carbon atoms.

The term aryl, when used alone or in combination, refer to an aromatic ring containing six to ten ring carbon atoms. The aryl group includes phenyl, and 1- or 2-naphthyl. The preferred aryl group is phenyl.

The term aralkyl refers to aryl groups as described above which have alkyl groups as ring substituents. The most preferred aralkyl group is benzyl.

As used herein, lower alkoxy refers to a lower alkyl group having at least one hydroxyl substituent. Halo refers to the halogen compounds, especially bromine, iodine, chlorine and fluorine.

The term lower carboxyalkylene refers to groups having the formula

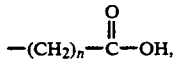

where n may vary from 1 to 5. Representative groups include carboxymethylene, carboxyethylene, carboxypropylene, carboxybutylene, and carboxypentylene. The alkalene groups may, optionally, be branched. Especially preferred are carboxymethylene, carboxyethylene, and carboxypropylene.

A chelating moiety is herein defined to be any acidic group, including groups from Lewis acids, capable of forming a complex with the metal ions of the present invention. Such moieties include carboxylic acids, phosphoric acids, amines and the like.

The term saturated hydrocarbon chain refers to an alkyl chain which contains no double or triple bonds. Examples of chains contemplated for use herein include myristyl, palmityl, lauryl, stearyl, caproyl, capryl, caprylyl, arachidyl, melissyl and the like. An unsaturated hydrocarbon chain contains at least one double bond or triple bond and may contain several such bonds. Examples of unsaturated hydrocarbon chains as contemplated herein include oleyl, myristoleyl, palmitoleyl, elaidyl, linoleyl, arachidonyl, γ-linolenyl and the like.

Preferred compounds of the invention are those wherein one or two of the substituents $R_1-R_4$ and X are

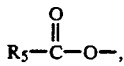

with $R_5$ being a saturated or unsaturated hydrocarbon chain having 6 to 30 carbon atoms, and more preferably 8 to 24 carbon atoms. These preferred compounds should also have a sufficient number of complexing acid groups available for chelating at least one metal ion. For example, such chelating groups may be two or more carboxylates or chelating moieties as defined herein. The complexing acid groups thus are provided by the non-lipophilic $R_1-R_4$ and X groups, or when one of these groups is defined as $-CONR_7R_8$, then $R_7$ and $R_8$ may provide the complexing acid groups.

Preferred compounds are those wherein a is 0 or 1, and b is 1 to 5, more preferably 1 to 3.

When a is 0, preferred compounds are those where R is hydrogen; $R_1$ is

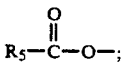

$R_3$ is hydroxyl; and $R_2$ and $R_4$ are $-CONR_7R_8$ with $R_7$ and $R_8$ being lower carboxyalkylene, especially carboxymethylene. Other preferred compounds, having a equal to 0, are those wherein R is hydrogen; $R_1$ and $R_3$ are

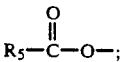

and $R_2$ and $R_4$ are $-CONR_7R_8$ with $R_7$ and $R_8$ being lower carboxyalkylene, especially carboxymethylene.

When a is 0 or 1, further preferred compounds include those where R is hydrogen; $R_1$ is

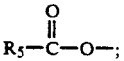

and $R_2$, $R_3$, $R_4$ and X are $-COOR_6$ or a chelating moiety with a sufficient number of $R_6$ groups, if present, being hydrogen to provide the needed metal ion(s) chelating moieties. Still further preferred compounds provided by the subject invention are those where R is hydrogen; X is

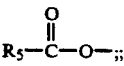

and $R_1$, $R_2$, $R_3$, and $R_4$ are $-COOR_6$ or a chelating moiety, again with sufficient $R_6$ groups being hydrogen, if present, so that metal ion(s) can be chelated.

The especially preferred compounds of the invention are listed below:

N-(2-myristoyloxyethyl)-N'-(2-hydroxyethyl)-N,N'-bis[N'',N'''-bis(carboxymethyl)acetamido]-1,2-ethanediamine, N,N'-bis(2-myristoyloxyethyl)-N,N'-bis[N'',N'''-bis(carboxymethyl)acetamido]-1,2-ethanediamine, N-(3-myristoyloxypropyl)diethylenetriamine-N,N',N'',N'''-tetraacetic acid, and N-(3-myristoyloxypropyl)-N,N-bis[2-[N',N'-bis (carboxymethyl)nitrilo]ethyl]amine.

The compounds of the invention can be prepared by art recognized methods. For example, compounds having acetamide substituents can be prepared by alkylating

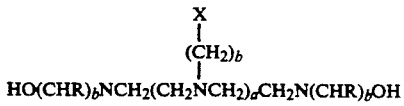

with a haloacetamide (with the acetamide group being substituted with an aralkyl carboxyalkylene if desirable) followed by monoaralkyloxycarbonylation on one of the hydroxyl groups and acylation of the other to obtain a monoacylated agent. Diacylation can be done directly after alkylation. In either case, the aralkyl groups of the carboxylates are removed by catalytic hydrogenation to obtain the complexing acid.

One specific synthetic route available to produce two of the preferred compounds is described and illustrated in Scheme 1 below (compound numbers are as defined in the Examples).

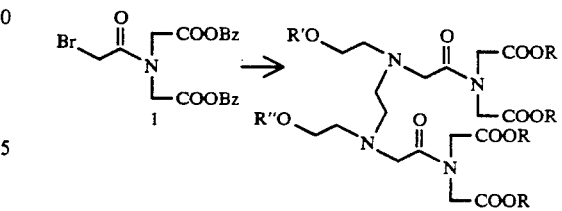

2 R' = R'' = H, R = Bz
3 R' = Myristoyl, R'' = COOBz, R = Bz
4 R' = R'' = Myristoyl, R = Bz
5 R' = Myristoyl, R'' = R = H
6 R' = R'' = Myristoyl, R = H Intermediate 2 can be prepared by alkylation of N,N'-bis(2-hydroxyethyl)-ethylenediamine with compound 1. Direct monomyristoylation of compound 2 using stoichiometric amounts of myristoyl chloride can result in low yield and difficult chromatographic purification. Thus, following monobenzyloxycarbonylation on one of the hydroxyl groups in compound 2, the resulting monoacylated intermediate is subsequent treated with myristoyl chloride under dimethyl aminopyridine (DMAP) to give compound 3. Similarly, bismyristoylation of compound 2 affords compound 4 with 66% yield. Subsequently, debenzylation of 3 and 4 by catalytic hydrogenation lead to target compounds 5 and 6.

Other compounds of the invention represented by the formula

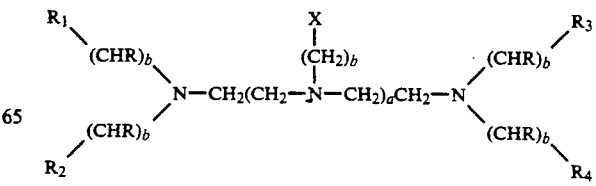

wherein $R_1$-$R_8$, X, a and b are as defined above, are also prepared by art recognized methods. For example, amino alcohols can be prepared by alkylation of

with an alkyl halide, and then further alkylated with aralkyl halocarboxyalkylenes to obtain an intermediate

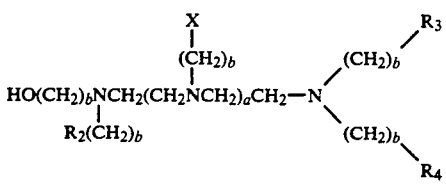

wherein X and $R_2$-$R_4$ are $COOR_9$ and $R_9$ is aralkyl (e.g. benzyl). The above compound can be acylated, preferably with an alkyl halide, followed by catalytic hydrogenation to remove the aralkyl groups and yield the desired compound. R groups can be introduced subsequent to the synthesis or by employing appropriately substituted alkylhalides or aralkyl halocarboxyalkylenes at the appropriate step. Moreover, similar production methods can be employed when the starting material is a compound of the formula

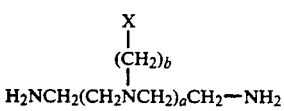

Alternately, a starting aminoalcohol of the formula

can be alkylated with iodoacetamide to form a tertiary amine which can be subjected to reduction of the keto group and further alkylation with an aralkyl halocarboxyalkylene. Acylation and catalytic hydrogenation are then conducted as before, to yield the desired compounds.

To illustrate a synthetic route to two preferred compounds of this invention are described below and illustrated in Scheme II (the compound numbers refer to those used in the Examples).

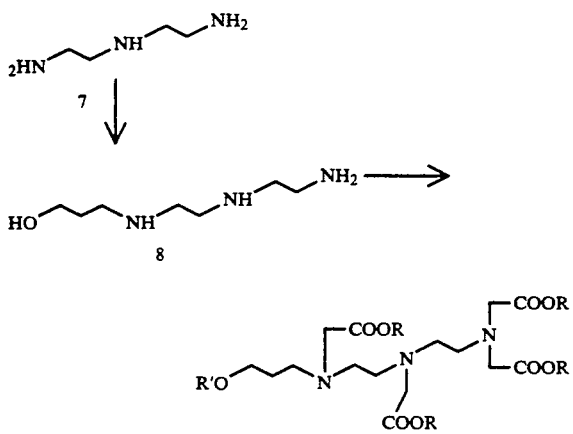

9 R' = H, R = Bz

10 R' = Myristoyl, R = Bz
11 R' = Myristoyl, R = H

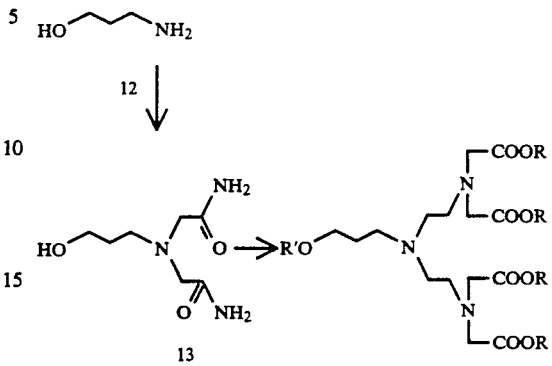

14 R' = H, R = Bz
15 R' = Myristoyl, R = Bz
16 R' = Myristoyl, R = H

Specifically, ligand 11 can be obtained by alkylation of diethylenetriamine with chloropropanol and benzyl bromo acetate, followed by acylation with myristoyl chloride and catalytic hydrogenation. For the preparation of ligand 16, alkylation of amino alcohol 12 with iodoacetamide is followed by borane reduction and treatment with benzyl bromoacetate to afford intermediate 14. Subsequently, acylation of compound 14 with myristoyl chloride and catalytic hydrogenation give compound 16.

The current enhancing agent comprises a metal ion selected from a member of the group consisting of paramagnetic metal ions, diamagnetic metal ions, ferromagnetic metal ions, or X-ray absorptive metal ions.

For NMR or MRI, the preferred metal ions employed in the agent of the present invention are paramagnetic metal ions since metal ions of this type generally have an enhanced relaxation effect on the surrounding water molecules in a mammalian host where the agent is taken up and generally, produce the enhanced contrast results in mammalian hosts. Paramagnetic metal ions by definition are those metal ions that carry unpaired electrons.

Ferromagnetic metal ions may also be employed in this respect and include those metal ions whose internal magnetic moments spontaneously organize in a common direction.

Diamagnetic metal ions may also be employed which are those metal ions that do not carry unpaired electrons. These metal ions position themselves at right angles to magnetic lines of force, and include for example, the alkaline earth metal ions (Group IIA of the Periodic Table of the Elements) and the alkali metal ions (Group IA of the Periodic Table of the Elements). The preferred alkaline earth metal ions comprise magnesium, calcium, strontium and barium, whereas the preferred alkali metal ions comprise lithium, sodium and potassium.

The preferred paramagnetic metal ions comprise the metal ions from the lanthanide group of the Periodic Table of the Elements and comprise those metal ions having atomic numbers 57-70 inclusive especially gadolinium and those metal ions having atomic numbers 21-29 inclusive and 42-44 inclusive especially copper, nickel, manganese, iron and chromium. Moreover, it is preferable that the metal ions are divalent or trivalent ions with suitable ions, for example, including chromium(III), manganese(II), iron(III), iron(II), cobalt(II), nickel(II), copper(II), praseodymium(III), neodymium(III), samarium(III) and ytterbium(III). Because of their very strong magnetic moments, gadolinium(III), terbium(III), dysprosium(III), holmium(III), and erbium(III) are preferred.

If the agents according to the invention are for use in X-ray diagnosis, the metal ion shall be derived from an element with a higher atomic number to achieve a sufficient absorption of X-rays. It has been found that contrast agents with metal ions of elements with atomic numbers of 57 to 83 inclusive are suitable for this purpose. These include, for example, lanthanum(III), the above mentioned ions of the lanthanide group, gold(III), lead(II) or, especially, bismuth(III).

All of the agents according to the invention, also intended for use both in NMR and X-ray diagnosis, are also suitable for use in ultrasonic diagnosis.

Production of the contrast agents are also known or can be performed fully conventionally as known in the art, e.g., in processes in which the metal oxide or a metal salt (for example, nitrate, chloride or sulfate) of an element with an atomic number of 21 to 29, 42 to 44 or 57 to 83 is dissolved or suspended in water and/or a lower alcohol (such as methyl, ethyl or isopropyl alcohol) and added to a solution or suspension of the equivalent amount of the complexing acid in water, a lower alcohol, or other suitable organic solvent (such as pyridine) and stirred, if necessary, with heating moderately or to the boiling point, until the reaction is completed. If the contrast agent that is formed is insoluble in the solvent that is used, it is isolated by filtering. If it is soluble, it can be isolated by evaporation of the solvent to dryness, for example, by spray drying.

If acid groups are still present in the resulting contrast agent, it is often advantageous to convert the acidic salt into a neutral salt by reaction with inorganic and/or organic bases or amino acids, which form physiologically biocompatible cations, and isolate them. In many cases, the procedure is even unavoidable since the dissociation of the complex salt is moved toward neutrality to such an extent by a shift in the pH value during the preparation that only in this way is the isolation of homogeneous products or at least their purification made possible. Neutralization is advantageously performed with organic bases or basic amino acids. It can also be advantageous, however, to perform the neutralization by means of inorganic bases (hydroxides, carbonates or bicarbonates) of sodium, potassium or lithium.

To produce the neutral salts, enough of the desired base can be added to the acidic contrast agents in an aqueous solution or suspension that the point of neutrality is reached. The resulting solution can then be concentrated to dryness in vacuo. It is often advantageous to precipitate the neutral salts by addition of solvents miscible with water, for examples, lower alcohols (methyl, ethyl, isopropyl alcohols, etc.), lower ketones (acetone, etc.), polar ethers (tetrahydrofuran, dioxane, 1,2-dimethoxyethane, etc.) and thus obtain crystallizates that isolate easily and purify well. It has been found particularly advantageous to add the desired bases to the reaction mixture even during complexing and thus eliminate a process stage.

If the acidic contrast agent contain several free acid groups, it is then often advantageous to produce neutral mixed salts which contain both inorganic and organic physiologically biocompatible cations as counterions. This can be done, for example, by reacting the complexing acids in an aqueous suspension or solution with the oxide or salt of the element supplying the metal ion and less than the full amount of an organic base necessary for neutralization, e.g., half, isolating the complex that is formed, purifying it, if desired, and then adding it to the amount of inorganic base necessary for complete neutralization. The sequence of adding the bases can also be reversed.

The contrast enhancing agents can be coupled as conjugates with biomolecules that are known to concentrate in an organ or part of an organ to be examined. Conjugates are also useful when the subject contrast agents are provided as shift reagents. These biomolecules include, for example, hormones such as insulin, prostaglandins, steroid hormones, amino sugars, peptides, proteins, lipids, etc. Conjugates with albumins, such as human serum albumin, or antibodies, for example, monoclonal antibodies specific to tumor-associated antigens, antimyosin, or exhibiting a desired diagnostic specificity provide a further battery of tools for diagnostic image analysis. For example, the diagnostic media formed therefrom are suitable for use in tumor and infarct diagnosis. Conjugates with liposomes, or by inclusion of the salts in liposomes, in both cases which, for example, are used as unilamellar or multilamellar phosphatidylcholine-cholesterol vesicles, are also suitable for diagnostic probes. The liposomes may be further modified to impart target specificity, i.e. attachment of antibodies, hormones, peptides, proteins and the like. Conjugating can be conventionally effected either via a carboxyl group of the complexing acid, and in the case of proteins especially to amino or thiol linkages. Moreover, several acid radicals can be partially bonded to the macromolecular biomolecule in the conjugation of the complex salts with proteins, peptides or lipids. In this case, each complexing acid radical can carry a metal ion. If the complexing acids are not bonded to biomolecules, they optionally carry two metal ions usually and especially one metal ion.

Liposomes are formed by conventional means and these techniques are well known and widely available to the ordinary-skilled artisan. One example of liposome formation is described by Grant G. W. M. et al. (1989) *Magn. Reson. Med.* 11: 236. Any lipid such as the phospholipids of phosphatidylcholine, phosphatidylserine, phosphatidylethanolamine, phosphatidylinositol, cardiolipins, lysophospholipids, or other lipids such as glycolipids, sphingolipids, fatty acids, and glycerides (mono, di or tri) are suitable for incorporation into liposomes. Moreover, the liposomes may contain other components such as cholesterol or protein. When protein is present, the liposomes are proteoliposomes. Further, the chain lengths of the lipids can be varied as desired, for example as herein described in the definition of $R_5$.

For the subject invention liposomes having the contrast enhancing agents incorporated therein may be prepared by the methods of Kalbalka, G. W. et al. (1988) *Magn. Reson Med.* 8:89 as modified by Grant et al.

Another aspect of the present invention is directed to a method for diagnostic analysis by administering the subject contrast enhancing agents or conjugates thereof to a host, preferably a mammalian host, in an amount sufficient to effect the desired contrast (or shift) and then subjecting the host to diagnostic analysis. Preferably diagnostic analysis is NMR analysis; including and especially preferred, NMR imaging analysis (or MRI).

Further, the subject compounds are useful in diagnostic analysis by X-ray image analysis or ultrasonic analysis. While described primarily as contrast enhancing agents, the subject agents can act as NMR shift reagents and such use is contemplated by the methods herein.

The subject contrast enhancing agents are administered in an amount sufficient to effect the desired contrast. For NMR, this amount is an NMR signal affecting amount of said agent, i.e., any amount of said agent that will alter the spin-lattice, spin-spin or spin-echo relaxation times of an NMR signal or for a shift reagent, selectively shift the spectral position of a resonant nucleus relative to other similar nuclei. This alteration is effected in a manner in order to enhance the signals received from the specimen under analysis either by reducing the aforementioned relaxation times or by increasing them with respect to an area of the host or the host per se which has had the complex administered to it. Shift reagents thus also distinction of signals in a specimen. In another embodiment, the NMR signal affecting amount of said agent is that amount which in addition to changing the relaxation times of the NMR signals in the host, will also change such relaxation times sufficiently so that sharper lines of definition or higher contrast is obtained between those parts of the host that have and have not been administered the complex.

The relaxation time $T_1$ (called the spin lattice) measures the rate at which magnetic energy is transferred from the resonant nuclei to all other energetic degrees of freedom excluding other resonant nuclei. The relaxation time $T_2$ (spin-spin) measures the rate of magentization transfer to other resonant nuclei.

Another parameter which can be measured is the density p (rho) of the protons in the medium. As a first approximation, it represents the quantity of free water contained in the sample.

The image by nuclear magnetic resonance represents the distribution of these parameters p, $T_1$, $T_2$ or their combination. The contrast between a given tissue and the adjacent tissues increases as a function of the tissues containing more or less water or mobile protons and differing relaxation times. It is also possible to modify the contrast by varying one or more of these parameters. Experience has shown that it was of greater interest to modify the relaxation time to improve the contrast of the image which can be accomplished, for example, with contrast enhancing agents provided herein. The density of the protons (in practice those of water and lipids) varies little between individual organs and often less between normal and pathological tissues. However, the relaxation characteristics are dependent on a larger number of factors (microscopic dynamics of the molecules, chemical exchange, paramagnetic disturbances, etc.), which are much more variable. The at least relative technical possibilities of selecting different parameters for obtaining the final image (experimentally echoes of spins aiding the function of $T_2$, or experimentally reversal-recovery of the magnetization permitting the local measurement of $T_1$) have shown the significance of the method.

A detailed discussion of NMR and theoretical considerations in selecting the appropriate parameters for diagnostic analysis is rendered in U.S. Pat. No. 4,749,560 which is incorporated herein by reference, e.g. CAT scans, X-ray image analysis and ultrasonic diagnosis are conducted in accordance with well-established techniques.

Moreover, the present method of diagnostic analysis allows tissue-or organ-specific diagnostic analysis to be achieved. For example, the subject contrast enhancing agents can exhibit organ and tissue specificity, e.g., bidifferential distribution, especially in myocardial tissue since these agents exhibit a lipophilic nature. Further specificity can be gained when the subject contrast enhancing agents are conjugated to molecules which themselves exhibit target specificity as described hereinbefore. All such variations of the present methods are contemplated by the invention.

The present contrast agents may be administered to a host as a pharmaceutical composition in a contrast-enhancing amount. The pharmaceutical compositions contain a contrast-enhancing dosage of the contrast agents according to the invention together with a pharmaceutically acceptable carrier. The compositions can be administered by well-known routes including oral, intravenous (if soluble) intramuscular, intranasal, intradermal, subcutaneous, parenteral, enteral and the like. Depending on the route of administration, the pharmaceutical composition may require protective coatings.

The pharmaceutical forms suitable for injectionable use include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water, buffered aqueous solutions (i.e., biocompatible buffers), ethanol, polyol (glycerol, propylene glycol, polyethylene glycol and the like), suitable mixtures thereof, surfactants or vegetable oils. Sterilization can be accomplished by any art recognized technique, including but not limited to, addition of antibacterial or antifungal agents, for example, paraben, chlorobutanol, phenol, sorbic acid, thimerosal, and the like. Further, isotonic agents, such as sugars or sodium chloride may be incorporated in the subject compositions.

Production of sterile injectable solutions containing the subject contrast agent is accomplished by incorporating these agents in the required amount in the appropriate solvent with various ingredients enumerated above, as required, followed by sterilization, preferably filter sterilization. To obtain a sterile powder, the above solutions are vacuum-dried or freeze-dried as necessary.

When the contrast agents are administered orally, the pharmaceutical compositions thereof containing an effective dosage of the contrast agent, may also contain an inert diluent, an assimilable edible carrier and the like, be in hard or soft shell gelatin capsules, be compressed into tablets, or may be in an elixir, suspension, syrup or the like.

The subject contrast agents are thus compounded for convenient and effective administration in pharmaceutically effective amounts with a suitable pharmaceutically acceptable carrier in a dosage which affects contrast enhancement. These amounts are preferably about 1 μmole to 1 mole of the contrast agent per liter and are administered in doses of about 0.001 to 5 mmole/kg body weight. Preferred compositions provide effective dosages of contrast agents in the range of about 0.001-5 mmole/kg for NMR diagnostics, preferably about 0.005-0.5 mmole/kg; in the range of about 0.1-5 mmole/kg for X-ray diagnostics; and in the range of about 0.1-5 mmole/kg for ultrasound diagnostics.

As used herein, a pharmaceutically acceptable carrier includes any and all solvents, dispersion media, coatings, antibacterial and antifungal agents, isotonic agents, and the like. The use of such media and agents are well-known in the art.

The following Examples further illustrate the invention.

EXAMPLE 1

Materials and Methods

Melting points were determined in open capillaries with a Gallenkamp melting point apparatus and are uncorrected. High resolution proton NMR spectra to confirm intermediates and identify products, were recorded on a Bruker AM-360 instrument. Either Me$_4$Si (CDCl$_3$, DMSO-d$_6$) or 3-(trimethylsilyl)-propionic-2,2,3,3-d$_4$ acid, sodium salt (TSP) (D$_2$O) were used as internal standard. Chemical shifts (in ppm) are reported along with peak muliplicities: br, broad; m, multiplet; t, triplet; d, doublet; s, singlet. Elemental analyses were performed by Atlantic Microlab Inc. Norcross, Ga.

EXAMPLE 2

A. N,N-Bis(benzyloxycarbonylmethyl)-bromoacetamide (1): A solution of dibenzyl iminodiacetate (9.7 g, 0.031 mol) and triethylamine (4.05 g, 0.04 mol) in 30 ml of carbon tetrachloride was added dropwise to a solution of bromoacetyl bromide (8.88 g, 0.044 mol) in 20 ml of carbon tetrachloride at 0° C. and stirring was continued for 30 min. After addition of water, the organic layer was washed with saturated-NaHCO$_3$ solution and saturated-brine, dried with MgSO$_4$, filtered and concentrated under reduced pressure. The residue was purified by flash column chromatography [silica gel, hexane:EtOAc (3:1)] and yielded 12.66 g (94%) of Compound 1; NMR (CDCl$_3$): δ3.86 (s,2H), 4.25 (s,2H), 5.15 (s,2H), 5.19 (s,2H), 7.3–7.5 (m, 10H).

B. N-(2-Myristoyloxyethyl)-N'-(2-benzyloxycarbonyloxyethyl)-N,N-bis[N'',N'''-bis(benzyloxycarbonylmethyl) acetamido]-1,2-ethanediamine(3): A suspension of N,N'-bis(2-hydroxyethyl)-ethylenediamine (0.8 g, 0.0054 mol) and triethylamine (1.27 g, 0.012 mol) in 5 ml of DMF was treated with a solution of bromo compound 1 (5.21 g, 0.012 mol) in 5 ml of DMF at 0° C. and stirring was continued for 2 h at room temperature. The reaction mixture was diluted with EtOAc and the organic solution was washed with 0.5 N-HCl, 0.5NNaOH and saturated brine. The organic layer was concentrated under reduced pressure affording an alkylated intermediate 2 used for the next step without any further purification. To a solution of compound 2 and DMAP (0.86 g, 0.007 mol) in 10 ml of dry THF a solution of benzyl chloroformate (1.2 g, 0.007 mol) in 5 ml of dry THF was added dropwise at 0° C. and stirring was continued for 1 h at the same temperature and for 2h at room temperature. Subsequently, the reaction mixture was treated with a solution of DMAP (0.86 g, 0.007 mol) in 10 ml of dry THF, followed by dropwise addition of a solution of myristoyl chloride (1.61 g, 0.0065 mol) in 10 ml of dry THF. After stirring the reaction mixture at room temperature overnight, the reaction mixture was diluted with chloroform and the organic layer was washed with saturated brine. Purification through a silica gel column using hexane:EtOAc:methanol (16:4:1) as eluent afforded 3.17 g (49%) of compound 3. NMR (CDCl$_3$): δ0.88 (t,3H), 1.24 (s,20H), 1.5–1.7 (m, 4H), 2.23 (t,2H), 2.61 (s,4H), 2.71 (t,2H), 2.76 (t,2H), 3.40 (s,2H), 3.41 (s,2H), 4.03 (t,2H), 4.11 (t,2H), 4.16 (s,4H), 4.38 (s,2H), 4.41 (s,2H), 5.1–5.2 (m,10H), 7.2–7.4 (m,25H).

C. N-(2-Myristoyloxyethyl)-N'-(2-hydroxyethyl)-N,N'-bis[N'',N''-bis(carboxymethyl)acetamido]-1,2-ethanediamine (5): A solution of compound 3 (2.15 g, 1.79 mmol) in 50 ml of ethanol was hydrogenated over 10% palladium on carbon at 45 psi overnight. The reaction mixture was filtered and concentrated under reduced pressure. The residue was recrystallized from ethanol affording 0.92 g (73%) of compound 5. NMR (20% K$_2$CO$_3$ in D$_2$O): δ0.88 (t,3H), 1.28 (brs, 20H), 1.5–1.7 (m,2H), 2.36 (t,2H), 2.5–3.0 (m,8H), 3.4–3.5 (m,4H), 3.64 (t,2H), 3.90 (2,6H), 4.20 (s,4H).

EXAMPLE 3

A. N,N'-Bis(2-Myristoyloxyethyl)-N,N'-bis[N'',N''-bis(benzyloxycarbonylmethyl)acetamido]-1,2-ethanediamine(4): A solution of compound 2 and DMAP (1.59 g, 0.013 mol) in 25 ml of dry THF was treated with a solution of myristoyl chloride (3.21 g, 0.013 mol) in 15 ml of dry THF and the resulting solution was stirred at room temperature overnight. The mixture was diluted with chloroform and water. The organic layer was washed with saturated NaHCO$_3$ solution and saturated brine, dried with MgSO$_4$, filtered and concentrated under reduced pressure. Purification [silica gel, hexane: EtOAC (2:1)] afforded 4.55 g (66%) of compound 4. NMR (CDCl$_3$): δ0.88 (t,6H), 1.25 (brs,40H), 1.56 (t,4H), 2.24 (t,4H), 2.62 (s,4H), 2.72 (t,4H), 3.41 (s,4H), 4.05 (t,4H), 4.18 (s,4H), 4.43 (s,4H), 5.12 (s,4H), 5.15 (s,4H), 7.2–7.4 (m,20H).

B. N,N'-Bis(2-Myristoyloxyethyl)-N,N'-bis[N'',N''-bis(carboxymethyl)acetamido]-1,2-ethanediamine(6): was prepared by the methodology analogous to that employed in the preparation of compound 5. Thus, compound 4 (2.28 g, 1.79 mmol) was catalytically hydrogenated under the conditions employed in Example 2C and yielded 1.15 g (70%) of compound 6. NMR (20% K$_2$CO$_3$ in D$_2$O): δ0.88 (t,6H), 1.29 (brs,40H), 1.5–1.7 (m,4H), 2.38 (t,4H), 2.7–3.1 (m,8H), 3.52 (brs,4H), 3.91 (brs,8H), 4.20 (t,4H).

EXAMPLE 4

A. Tetrabenzyl N-(3-hydroxypropyl)diethylenetriamine-N,N',N'',N''-tetraacetate(9): A solution of aminoalcohol 8 (4.03 g, 0.025 mol) [Timakova, L. M. et al. (1977) Zh. Obsh. Khim. 47: 691] and triethylamine (12.65 g, 0.125 mol) in 35 ml of DMF was added dropwise to a cold (0° C.) solution of benzyl bromoacetate (28.64 g, 0.125 mol) in 25 ml of DMF during a period of 1 h, and the resulting mixture was stirred overnight at room temperature. After partition of the mixture between EtOAc and water, the organic layer was washed with saturated brine, dried with MgSO$_4$, filtered and concentrated under reduced pressure. The residue was purified through silica gel column using EtOAc:hexane (3:1) as eluent, affording 8.6 g (46%) of compound 9. NMR (CDCl$_3$): δ1.5–1.7 (m,2H), 2.6–2.9 (m,10H), 3.38 (s,2H), 3.47 (s,2H), 3.60 (s,4H), 3.70 (t,2H), 4.88 (brs, 1H), 5.09 (s, 2H), 5.10 (s,4H), 5.11 (s,2H), 7.33 (s,20H).

B. Tetrabenzyl N-(3-Myristoyloxypropyl)diethylene triamine-N,N',N'',N''-tetraacetate(10): To a solution of hydroxyester 9 (1.13 g, 1.5 mmol) and triethylamine (0.18 g, 1.8 mmol) in 7 ml of carbon tetrachloride, a solution of myristoyl chloride (0.45 g, 1.8 mmol) in 10 ml of carbon tetrachloride was added at 0° C. and the resulting solution was stirred overnight at room temperature. The CCl$_4$ layer was washed with saturated brine and concentrated. The residue was purified by silica gel column chromatography [hexane: EtOAc (2:1)] affording 0.83 g (57%) of compound 10. NMR (CDCl$_3$): δ0.88 (t,3H), 1.25 (brs,20H), 1.5–1.8 (m,4H), 2.25 (t,2H), 2.5–3.0 (m,8H), 3.39 (s,2H), 3.45 (s,2H), 3.61 (s,4H), 4.04 (t,2H), 5.10 (s,8H), 7.33 (brs,20H).

C. N-(3-Myristoyloxypropyl)diethylenetriamine-N,N',N",N"'-tetraacetic acid(11): A solution of benzyl ester 10 (0.73 g, 0.76 mmol) in 10 ml of EtOH was hydrogenated over 10% Pd/C(0.1 g) at 45 psi overnight. The residue was recrystallized from EtOH yielding 0.19 g (41.6%) of target 11. NMR (20% K$_2$CO$_3$ in D$_2$O): δ0.88 (t,3H), 1.27 (brs,20H), 1.56 (m,2H), 1.83 (m,2H), 2.34 (t,2H), 2.5–2.8 (m,10H), 3.0–3.3 (m,8H), 4.09 (t,2H).

EXAMPLE 5

A. N-(3-Hydroxypropyl)-iminodiacetamide(13): A solution of 3-amino-1-propanol (1.88 g, 0.025 mol) and triethylamine (6.33 g, 0.063 mol) in 20 ml of dry acetonitrile was added to a suspension of iodoacetamide (9.71 g, 0.053 mol) in 35 ml of dry acetonitrile at 0° C. and the resulting solution was stirred for 1 h at 0° C. followed by stirring overnight at room temperature. The solid in the reaction mixture was collected, washed with hot chloroform and recrystallized from THF affording 2.69 g (57%) of compound 13. NMR (D$_2$O): δ1.7–1.8 (m,2H), 2.67 (t,2H), 3.29 (s,4H), 3.65 (t,2H).

B. N-(3-Hydroxypropyl)-N,N-bis[2-[N',N'-bis(benzyloxycarbonylmethyl)nitrilo]ethyl]amine(14): To a suspension of amide 13 (2.518 g, 0.0133 mol) in 50 ml of dry THF, 130 ml of BH$_3$ THF was added dropwise at 0° C., and the resulting mixture was stirred overnight. Methanol (20 ml) was added to the reaction mixture at 0° C. After evaporation of the solvent, the residue was dissolved in methanol and saturated with HCl gas, followed by reflux of the reaction solution for 2 h. The residue, obtained by the removal of methanol in 25 ml of DMF, was treated with Et$_3$N (15 ml) and the solid was removed by filtration. The filtrate was added to a solution of benzyl bromacetate (15.23 g, 0.0665 mol) in 15 ml of DMF at 0° C. and stirring was continued overnight. The reaction mixture was diluted with EtOAc and the organic solution was washed with saturated brine, dried with MgSO$_4$, filtered and concentrated under reduced pressure. Purification through a silica gel column using CHCl$_3$:methanol (15:1) as eluent afforded 4.98 g (50%) of compound 14. NMR (CDCl$_3$): δ1.5–1.6 (m,2H), 2.4–2.6 (m,6H), 2.85 (t,4H), 3.60 (s,8H), 3.67 (t,2H), 5.11 (s,8H), 7.2–7.4 (m,20H).

C. N-(3-Myristoyloxypropyl)-N,N-bis[2-[N',N'-bis(-benzyloxycarbonylmethyl)nitrilo]ethyl]amine(15): Compound 15 was prepared in the same way as described for the preparation of compound 10 beginning with compound 14 (see Example 4B). Thus, compound 14 (1.51 g, 2 mmol) gave 0.98 g (51%) of compound 15. NMR (CDCl$_3$): δ0.88 (t,3H), 1.25 (brs,20H), 1.6–1.8 (m,4H), 2.26 (t,2H), 2.4–2.9 (m,10H), 3.56 (s,8H), 4.01 (t,2H), 5.12 (s,8H), 7.3–7.4 (m,20H).

D. N-(3-Myristoyloxypropyl)-N,N-bis[2-[N',N'-bis(-carboxymethyl)nitrilo]ethyl]amine(16): Compound 16 was prepared from 15 according to the procedures described for the preparation of 11 from 10 (see Example 4C) affording 0.31 g (67%) as a white solid. NMR (20% K$_2$CO$_3$ in D$_2$O): δ0.88 (t,3H), 1.28 (brs,20H), 1.5–1.7 (m,2H), 1.8–2.0 (m,2H), 2.36 (t,2H), 2.5–2.9 (m,10H), 3.1–3.4 (m,8H), 4.1 (t,2H).

EXAMPLE 6

Preparation of Gd Complexes of Compounds 5 and 6

Gd complexes of target compounds 5 and 6 were prepared according to the procedure of Kabalka, et al. Thus a solution of GdCl$_3$ 6H$_2$O(0.39 g, 1.05 mmol) in 2 ml of distilled water was added dropwise to a solution of compound 5 (0.494 g, 0.7 mmol) in 25 ml of pyridine and stirring was continued for 30 min at room temperature. The solvent was completely removed under reduced pressure and the residue was suspended in distilled water to remove excess GdCl$_3$. The solid in water was collected by filtration and dried under vacuum affording 0.626 g (96%) of Gd complexed compound 5. Anal. calcd. for C$_{32}$H$_{53}$N$_4$O$_{13}$Gd 4H$_2$O: C, 41.28; H, 6.60; N, 6.02. Found: C, 41.21; H, 6.46; N, 5.81.

Similarly, compound 6 (0.641 g, 0.7 mmol) yielded 0.706 g (91%) of Gd complexed compound 6. Anal. calcd. for C$_{46}$H$_{79}$N$_4$O$_{14}$Gd 2H$_2$O: C,49.98; H, 7.57; N, 5.07. Found: C, 49.89; H, 7.65; N, 5.00.

EXAMPLE 7

Gd complexes with compound 11 and 16 were prepared as described in Example 6.

EXAMPLE 8

Incorporation of Gd Complexes 5 and 6 in Liposomes

Liposomes were prepared by the procedure of Kabalka et al., as modified by Grant, et al., by mixing either 4.7 mg of Gd complex 5 or 5.6 mg of Gd complex 6, 2 mg of cholesterol and 20 mg of egg lecithin (20 mg/ml in chloroform molar ratio 1:1:5, Avanti Co.) in 8 ml of chloroform and methanol (2:1). N$_2$ gas was introduced into the mixture to remove the solvent and the residue was dried for 2 days under vacuum. The resulting dry lipids were suspended in 5 ml of 0.9% saline solution (pH 7.0) affording a 1 mM solution of the Gd complex. The suspension was sonicated for 2 h at 4° C. A Branson Model W-350 sonifier with a microtip probe was used with the power setting in pulsed mode (50% duty cycle) at 3. Subsequently, the liposomes were centrifuged at 2000 rpm for 30 min at 4° C. to remove titanium particles generated by the sonicator probe tip. The supernatant solution of the liposomes was used for measurement of relaxivities.

EXAMPLE 9

NMR Relaxivity Measurements

The 1:1 complexes of Gd$^{3+}$ with compounds 5, 6, 11 and 16 as ligands were used for water proton NMR relaxation rate (1/T$_1$) measurements at pH 7.0 as a function of the concentration of each complex (0.2–1.0 mM) on IBM PC-10 (10 MHz, 0.23T) and IBM PC-20 (20 MHz 0.47T) Multispec NMR instruments. 1/T$_1$ measurements were taken at a probe temperature of 40° C. The average of two consecutive 1/T$_1$ measurements is taken as the final relaxation rate value. From the slope of 1/T$_1$ vs [Gd complex], the relaxivity of each complex is determined. The resulting relaxivities are presented in Table 1. The relaxivities of 5 and 6 are significantly larger than those of Gd(EDTA) and Gd(DTPA) and are similar to those of uncomplexed Gd$^{3+}$ aquoion [Lauffer, R. B. et al. (1985) *Magn. Reson. Imaging* 3: 11; Koenig, S. H. et al. (1984) *Mag. Reson. Med.* 1496]. The relaxivities of 11 and 16, however, are similar to those of Gd(EDTA) and Gd(DTPA). Relaxativities of compounds 5 and 6 increase from 0.23T to 0.47T, whereas those of compounds 11 and 16 decrease with increasing magnetic field. When complexes 5 and 6 are incorporated into liposomes, a 51-86% increase of relaxivity at both magnetic fields was observed.

TABLE 1

| Compound | Relaxivity (sec$^{-1}$ mM$^{-1}$) | |
|---|---|---|
| | 0.23 T | 0.47 T |
| 5 | 9.7 | 13.6 |
| 6 | 11.2 | 14.3 |
| 11 | 5.5 | 4.9 |
| 16 | 8.6 | 7.8 |
| 5 + Liposomes | 17.9 | 25.4 |
| 6 + Liposomes | 17.0 | 24.8 |

We claim:

1. A method for X-ray image analysis or ultrasonic analysis comprising administering to a host a contrast enhancing amount of a contrast enhancing agent which comprises a complexing acid or a salt thereof and at least one metal ion of an element with an atomic number 21 to 29, 42 to 44 or 57 to 83, wherein said acid has the formula

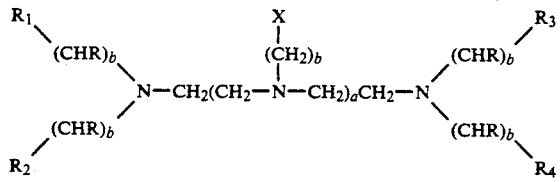

wherein
a is 0 to 5;
b is 1 to 5;
each of a and b can be the same or different;
each R is hydrogen, lower alkyl, hydroxy, halo, lower alkyoxy, aryl, or lower aralkyl; at least one of $R_1$, $R_2$, $R_3$, $R_4$ or X has the formula

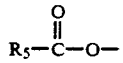

wherein $R_5$ is a saturated or unsaturated hydrocarbon chain having 6 to 30 carbon atoms; and the others of $R_1$, $R_2$, $R_3$, $R_4$, or X are hydrogen, hydroxyl, —COOR$_6$, —CONR$_7$R$_8$ or a chelating moiety
wherein $R_6$, $R_7$, and $R_8$ are the same or different and represent hydrogen, lower alkyl, lower alkoxy, lower carboxyalkylene, or a chelating moiety;
and subjecting said host to X-ray image analysis or ultrasonic analysis.

2. The method of claim 1 wherein said host is a mammal.

3. The method of claim 1, wherein $R_5$ is a hydrocarbon chain substituted with a lower alkyl, hydroxyl, lower alkoxy or halogen moiety.

4. The method of claim 1, wherein $R_5$ is a saturated alkyl chain having 6 to 30 carbon atoms.

5. The method of claim 4, wherein said alkyl chain has 8 to 24 carbon atoms.

6. The method of claim 1, wherein

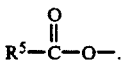

7. The method of claim 6, wherein R is hydrogen, $R_2$, $R_3$, $R_4$ and X are COOR$_6$, and $R_6$ is hydrogen.

8. The method of claim 1 wherein X is

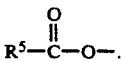

9. The method of claim 8 wherein R is hydrogen, $R_1$, $R_2$, $R_3$ and $R_4$ are COOR$_6$, and $R_6$ is hydrogen.

10. The method of claim 6 wherein R is hydrogen, $R_2$ and $R_4$ are —CONR$_7$R$_8$, $R_3$ is hydroxyl, and $R_7$ and $R_8$ are lower carboxyalkylene.

11. The method of claim 10, wherein a is 0.

12. The method of claim 1 wherein $R_1$ and $R_3$ are

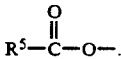

13. The method of claim 12 wherein R is hydrogen, $R_2$ and $R_4$ are COOR$_6$, and $R_6$ is hydrogen.

14. The method of claim 13 wherein a is 0.

15. The method of claim 12 wherein R is hydrogen, $R_2$ and $R_4$ are —CONR$_7$R$_8$ and $R_7$ and $R_8$ are lower carboxyalkylene.

16. The method of claim 15 wherein a is 0.

17. The method of claim 1 wherein said complexing acid is N-(2-myristoyloxyethyl)-N'-(2-hydroxyethyl)-N,N'-bis[N'',N''-bis(carboxymethyl)acetamido]-1,2-ethanediamine.

18. The method of claim 1 wherein said complexing acid is N,N'-bis(2-myristoyloxyethyl)N,N'-bis[N'',N''-bis(carboxymethyl)acetamido]-1,2-ethanediamine.

19. The method of claim 1 wherein said complexing acid is N-(3-myristoyloxypropyl)diethylenetriamine-N,N',N'',N''-tetraacetic acid.

20. The method of claim 1 wherein said complexing acid is N-(3-myristoyloxypropyl)-N,N-bis[2-[N',N'-bis(carboxymethyl)nitrilo]ethyl]amine.

21. The method of claim 1 wherein said contrast enhancing agent is conjugated to a biomolecule.

22. The method of claim 21 wherein said biomolecule is selected from the group consisting of hormones, prostaglandins, steroid hormones, amino sugars, peptides, proteins, liposomes, proteoliposomes, lipids, albumins and antibodies.

23. The method of claim 1 wherein said contrast enhancing amount is about 0.001 mmole to about 5 mmole of said agent per kilogram of said host.

* * * * *

UNITED STATES PATENT AND TRADEMARK OFFICE
CERTIFICATE OF CORRECTION

PATENT NO. : 5,242,681
DATED : September 7, 1993
INVENTOR(S) : Gabriel A. Elgavish, et al.

It is certified that error appears in the above-indentified patent and that said Letters Patent is hereby corrected as shown below:

Column 8, line 33: "current" should read --contrast--

Column 9, line 7: "arc" should read --are--

Column 11, line 28: "$T_1\measuredangle$" should read --$T_1$ (--

Column 18, line 5, Claim 6: after "wherein" insert -- $R_1$ is--

Signed and Sealed this

Seventh Day of June, 1994

Attest:

BRUCE LEHMAN

*Attesting Officer*  *Commissioner of Patents and Trademarks*